United States Patent
Romeo et al.

(10) Patent No.: US 9,919,198 B2
(45) Date of Patent: Mar. 20, 2018

(54) AUTOMATED PHYSICAL THERAPY SYSTEMS AND METHODS

(71) Applicant: Breg, Inc., Carlsbad, CA (US)

(72) Inventors: Steven Robert Romeo, Encinitas, CA (US); Geoffrey Scott Siegel, Carlsbad, CA (US); Robert Allyn Haywood, Jr., Carlsbad, CA (US); David R. Brengle, San Diego, CA (US)

(73) Assignee: Breg, Inc., Carlsbad, CA (US)

( * ) Notice: Subject to any disclaimer, the term of this patent is extended or adjusted under 35 U.S.C. 154(b) by 636 days.

(21) Appl. No.: 14/076,619

(22) Filed: Nov. 11, 2013

(65) Prior Publication Data

US 2015/0134088 A1 May 14, 2015

(51) Int. Cl.
| | |
|---|---|
| *G06Q 10/00* | (2012.01) |
| *G06Q 50/00* | (2012.01) |
| *A63B 71/06* | (2006.01) |
| *G06Q 50/22* | (2018.01) |

(52) U.S. Cl.
CPC ...... *A63B 71/0686* (2013.01); *A63B 71/0619* (2013.01); *G06Q 50/22* (2013.01)

(58) Field of Classification Search
CPC .............................. G06Q 50/22; G06Q 50/24
See application file for complete search history.

(56) References Cited

U.S. PATENT DOCUMENTS

| | | | | |
|---|---|---|---|---|
| 2007/0078710 | A1* | 4/2007 | Bender, II | G06Q 30/02 705/14.17 |
| 2008/0141135 | A1* | 6/2008 | Mason | G11B 27/034 715/719 |
| 2012/0259652 | A1* | 10/2012 | Mallon | G06F 19/3418 705/2 |
| 2013/0123667 | A1 | 5/2013 | Komatireddy et al. | |
| 2014/0081661 | A1* | 3/2014 | Fu | G06F 19/3481 705/3 |
| 2014/0170609 | A1* | 6/2014 | Hsiao | G09B 19/0092 434/127 |

* cited by examiner

*Primary Examiner* — Neha Patel
(74) *Attorney, Agent, or Firm* — Thomas A. Runk; Brooks Kushman P.C.

(57) ABSTRACT

A system for providing automated exercise management includes: a motion sensor configured to be worn by a user during a prescribed exercise routine and to sense motion of the user's body during the performance of the prescribed exercise routine; a first wireless communication interface communicatively coupled to the motion sensor; and a user computing device having a second wireless communication interface configured to communicate with the first wireless communication interface communicatively coupled to the motion sensor; wherein the user computing device comprises a processor, a memory and an application, wherein the application is configured to provide instruction to the user regarding performance of the prescribed exercise routine; receive data from the motion sensor worn by the user, the data indicative of the user's performance of the prescribed exercise; and record the user's performance of the exercise as indicated by the received data.

12 Claims, 11 Drawing Sheets

AUTOMATED PHYSICAL THERAPY SYSTEMS AND METHODS

TECHNICAL FIELD

The disclosed technology relates generally to the healthcare industry, and more particularly, some embodiments relate to systems and methods for automated physical therapy management.

DESCRIPTION OF THE RELATED ART

While computers and computerized systems have found their way into most of today's businesses, some sectors are more automated than others. For example, certain sectors of the healthcare industry have been slow to automate their systems and procedures, or have yet to evolve into an integrated, user-friendly computerized solution. This is true, for example, with a number of small healthcare practices, family practices, and hospital systems in this country and around the world. However, this shortcoming is not unique to small healthcare practices and indeed, many large healthcare practices suffer from a lack of automation with various aspects of the practice.

One area in particular that has been difficult for healthcare practices to manage is that of therapy in the home. Consider for example the case of physical therapy in which an injured patient is prescribed a regimen of exercises to improve his or her condition, or to regain use of injured appendages. In such scenarios, patients may fail to perform the prescribed exercises, or fail to perform them at the prescribed level (e.g., frequencies or number of repetitions). Likewise, patients may perform the exercises but may fail to carry them out properly. For example, the patient may fail to push to achieve the appropriate extension or range of motion prescribed. Additionally, even where a patient performs the exercises, the patient may fail to properly record the exercises or report back to the healthcare practice with the exercises accomplished or the results of those exercises. Because patients may fail to properly or fully complete the physical therapy at home, the potential for reduced outcomes from the surgical procedure is a real threat to the recovery process and may lead to additional incurred expense for surgical revision, which may drive up the overall cost of healthcare.

BRIEF SUMMARY OF EMBODIMENTS

According to various embodiments of the disclosed technology, a healthcare practice management system can be provided to assist managing the data flow and operation of healthcare practices, and to support the outcome of the patient. In some embodiments, a system for providing automated physical therapy management includes: a motion sensor configured to be worn by a user during a prescribed exercise routine and to sense motion of the user's body during the performance of the prescribed exercise routine; a first wireless communication interface communicatively coupled to the motion sensor; and a user computing device having a second wireless communication interface configured to communicate with the first wireless communication interface communicatively coupled to the motion sensor; wherein the user computing device comprises a processor, a memory and an application, wherein the application is configured to provide instruction to the user regarding performance of the prescribed exercise routine; receive data from the motion sensor worn by the user, the data indicative of the user's performance of the prescribed exercise; and record the user's performance of the exercise as indicated by the received data.

The system can further include a brace to be worn by the user during the prescribed exercise, wherein the motion sensor is attached to the brace during performance of the prescribed exercise. A health-care facility computing device can be included and configured to communicate with the user computing device, the health-care facility computing device comprising a processor, a memory and a second application, wherein the second application is configured to receive information regarding the user's performance of the prescribed exercise from the user computing device, and provide information to the user's health-care practitioner regarding the user's performance of the prescribed exercise. In various embodiments, the data indicative of the user's performance of the prescribed exercise as sensed by the motion sensor includes at least one of a number of repetitions of the prescribed exercise performed by the user, and a range of motion achieved by the user for one or more of said repetitions.

In further embodiments, the application is further configured to send the logged performance information to a health care practitioner. Sending the logged performance information to a health care practitioner can include sending information about the patient's performance as sensed by the motion sensor and logged by the application. The information about the patient's performance as sensed by the motion sensor can include a number of repetitions of the prescribed exercise performed by the user, and a range of motion achieved by the user for one or more of said repetitions.

In still further embodiments, the application may be further configured to provide the user an indication of success when the user completes an exercise in the prescribed physical therapy routine. The may also be further configured to use the data received from the motion sensor to measure patient performance against a benchmark.

In yet other embodiments, the application is configured to perform the operations of initiating an application on the client computing device, the application relating to a physical therapy routine to be performed by a user; communicatively coupling the client computing device with a motion sensor worn by the user; the application providing instruction to the user regarding performance of the physical therapy routine; receiving data from the motion sensor worn by the user, the data indicative of the user's performance of the physical therapy routine as sensed by the motion sensor; and logging information relating to the user's performance of the physical therapy routine as indicated by the received data.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Figure 1:
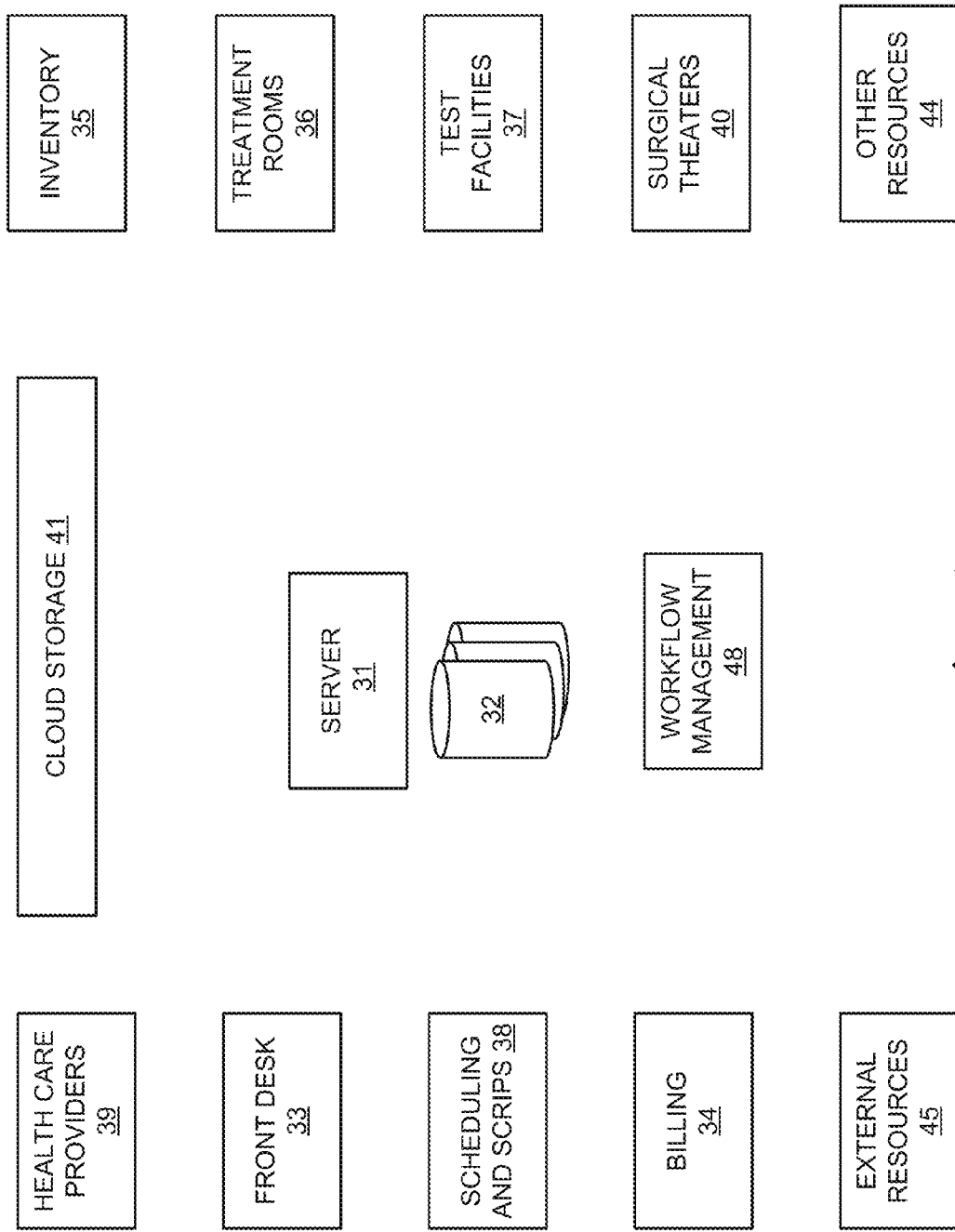
FIG. 1 is a diagram illustrating an example of a healthcare practice with which the disclosed technology may be implemented in accordance with one embodiment of the technology described herein.

The figures are not intended to be exhaustive or to limit the invention to the precise form disclosed. It should be understood that the invention can be practiced with modification and alteration, and that the disclosed technology be limited only by the claims and the equivalents thereof.

DETAILED DESCRIPTION OF THE EMBODIMENTS

The technology disclosed herein is directed toward systems and methods for automated physical therapy (including rehabilitation therapy) and physical therapy management. According to various embodiments, various aspects of a physical therapy program can be automated, and physical therapy data shared amongst the several components and systems within and external to the healthcare practice.

In various embodiments, the technology described herein may include an application running on a client device and used by a patient to instruct the patient on appropriate exercises to be performed for the physical therapy program, and to alert or remind the patient to perform the designated activities. In further embodiments, a detection apparatus such as an accelerometer or motion detector can be worn by the patient and used to sense the motion of the patient to help track performance of the prescribed activities or exercises in real time. The motion sensing apparatus can be configured to communicate data regarding the sensed activity to the device running the application. The application can use this information to track performance of the activity by the patient as well as to track the quality of the exercises performed by the patient. In other words, the motion sensor worn by the patient can measure movement of the patient or of a patient limb, sense the range of motion achieved during the activity or during each rep of the activity, provide information for each rep performed, and so on.

The application can use the information received from the motion sensor to keep track of whether the patient has performed the appropriate exercises at the appropriate intervals, performed the prescribed number of reps, achieved a desired range of motion during exercise, and otherwise performed according to the prescribed regimen. The application can cause this information to be stored on the client device and to be communicated to the caregiver or healthcare practitioner such that the patient's progress can be tracked regularly and, where desired, between office visits. Accordingly, the system can be configured to monitor the activity of the patient, measure the patient's performance during prescribed activities, record this information for record-keeping purposes, make this information available to the patient so he or she can track his or her own progress, and can communicate this information to a healthcare professional. The data can be presented to the patient and his or her health care provider in graphic, tabular, or other useful forms. The application can also be configured as a two-way communication tool. For example, the application in some embodiments can send information to the patient from the provider to send clinical notes, advice, or updates. The application can also be configured to allow patients to monitor their own progress through graphs, charts, and data gather, logged and analyzed through the patient application.

The following operational scenario illustrates and generally describes aspects of the technology set forth in this document. Typically, the process begins when the patient arrives at a physician's office (or the office of another healthcare professional) to receive treatment for injury. Upon arrival at the health care facility, the patient is greeted by an office coordinator in the physician's waiting room and is provided with an iPad, tablet or other computing device into which he or she may enter demographic data, data about his or her current and previous conditions and other relevant data. Additionally, electronic medical records brought to the office by the patient can be loaded into the iPad, tablet or other computing device to allow the patient medical records to be uploaded into the healthcare facility's databases.

Once the patient has completed the registration process, the patient meets with the healthcare practitioner to assess the condition and determine a procedure to treat the condition. Upon determining a procedure appropriate for the patient's condition, the physician coordinates the procedure. For example, surgery can be performed and the patient provided with a post-operative brace to be worn during the healing process. The physician can also provide direction to another healthcare practitioner, such as a trainer or physical therapist, to deliver a physical therapy solution for the patient.

The physical therapist (or other healthcare professional) logs into the healthcare facility's computing system to determine the workout routine for the patient's recovery. The healthcare facility may already have predefined protocols for various injuries and the healthcare practitioner may prescribe these predefined protocols for the patient. Alternatively, custom protocols can be defined for a given patient, entered into the computing system at the health care facility and made accessible to the practitioner. The trainer identifies the protocols appropriate for the patient and any additional exercises that may be recommended. Because the patient information has already been entered into the healthcare facility database, the trainer can easily identify the patient from a list of available patients and review any patient information necessary when identifying the physical therapy routines.

In some embodiments, the system generates a code that can be provided to the patient to use for downloading the physical therapy application. Preferably, the code is patient specific such that patient information and prescribed routines can be identified on a patient-by-patient basis, and patient unique information can be provided to the patient when he or she logs into the system. The code can be automatically e-mailed or text messaged to the patient based on patient information in the system. Alternatively, for privacy purposes the code can be provided to the patient directly at the time of the visit. An e-mail or other electronic message can also be sent to the patient with a link to download the application that the patient will use for the automated physical therapy routines.

When the patient logs onto the system and downloads the application, the patient code, or ID, identifies the patient to the healthcare facility computing system. In response, the healthcare computing system identifies the protocols (pre-built or custom) prescribed for the patient and provides those to the patient along with the application. Accordingly, delivery of the application includes delivery of protocols prescribed for the patient. Accordingly, the application can be configured to connect to the appropriate data storage (e.g. cloud storage) retrieve the appropriate physiotherapy routines for the patient as well as accompanying instructional videos and other information. The patient can then initiate the application and perform the physical therapy exercises under the guidance of the application.

The application can be configured to guide the patient through each step of the exercise. In some embodiments, the application can further be configured to present the exercises in a game-like fashion, which can help to keep the patient engaged with the exercise. Alerts can be provided to the healthcare practitioner informing the practitioner of the patient's progress or letting the practitioner know where the patient has failed to perform the prescribed exercises. When the patient achieves the prescribed protocols, the patient can receive an indication of success, which is also shared with the healthcare practitioner.

The computing systems at the healthcare facility can be used to monitor a large number of physical therapy episodes and monitor progress with an integrated view of all active patients. Because progress can be reported electronically and the data displayed graphically, it is easier for the healthcare practitioner to get a snapshot of his or her patient's progress. Additionally, surveys can be provided to the patient to obtain information about how the patient is feeling, about their strength, mobility, etc. This information is collected and can also be provided to the healthcare practitioner to facilitate assessment of the patient's progress and condition. Compliance and progress can be monitored for each patient as well as plotted data results of mobility versus survey-specific data demonstrating how the patient is feeling during recovery. This data can be combined in selected as desired to provide a graphic representation of the patient's recovery. The information can also be used in conjunction with insurance payors/billers to send supporting data with insurance claims to support the ACO (accountable care organization) and other billing models with outcomes data for the patient.

Before describing the technology in more detail, it is useful to describe an example environment in which the technology can be implemented. One such example is that of a medical or healthcare practice. FIG. 1 is a diagram illustrating an example of a healthcare practice with which the disclosed technology may be implemented. In general, the healthcare practice can include one or more medical practices such as, for example, an orthopedic medicine practice, a sports medicine practice, a pediatric practice, a general practitioner/family practice, and so on. The one or more medical practices can include physicians, physician assistants, nurse practitioners, radiologists, physical therapists and other healthcare professionals. The one or more medical practices can be located in a single facility or distributed across a plurality of facilities. With reference to FIG. 1, an exemplary healthcare practice can include one or more of a server 31, server data storage 32, a front desk 33, and a billing department 34, inventory 35, treatment rooms 36, test facilities 37, scheduling and prescriptions 38, one or more healthcare providers 39, one or more surgical theaters were operating rooms 40, cloud data storage 41, and other internal resources 44 and external resources 45.

Server 31 and its associated data storage 32 can be centralized or distributed, and can be configured to store any of a number of different types of data for the healthcare practice. This can include, for example, data such as patient records, including electronic health records (EHR); scheduling information; billing information; and other information and records used in the management, operation and maintenance of the healthcare practice. In addition to data storage 32, each of the other resource units in the healthcare practice can include its own computing and data storage capabilities. In addition to or in place of data storage 32 (and other data storage capabilities) cloud storage 41 can be provided to store data and information used in the healthcare practice. Cloud storage 41 can be configured to be accessible by server 31 as well as by other computing capabilities of the healthcare practice. Although one server 31 is illustrated, as would be apparent to one of ordinary skill in the art after reading this description, a number of different servers 31 can be provided in various logical and physical groupings.

Front desk 33 can be provided to greet and check-in patients at the healthcare facility. Depending on the size of the healthcare facility, front desk 33 may also be responsible for the functions of billing 34 and scheduling 38 as well as inventory 35. Billing 34 receives information regarding a patient visit, receives insurance and payment information from the patient, generates billing statements, records payments and tracks Accounts Receivable. The information regarding the patient visit used by billing 34 can include information such as, for example, the doctor or healthcare provider visited by the patient, supplies provided to or used in the treatment of the patient, articles delivered to the patient (e.g., a knee brace, crutches, etc.) and other information used to generate the bill. Inventory 35 can include supplies and other inventory used in the operation of the healthcare practice including inventory used in the treatment of patients. For example, in the case of an orthopedic practice, the inventory may include various elbow, knee, and other braces that may be provided or prescribed to a patient. The inventory may also include all other inventory (including consumables) used by the healthcare practice. Inventory levels can be tracked and managed electronically and the reordering of supplies can be automated. Scheduling and prescriptions 38 can be included to provide assistance with scheduling patient visits such as, for example, follow-on appointments, tests, and other events. Scheduling and prescriptions 38 can also manage patient prescriptions, which can include interfacing with pharmacies or other like fulfillment providers.

The healthcare practice generally includes one or more healthcare providers 39 to provide treatment and other services to the patients. Healthcare providers can include, for example, physicians, physician assistants, nurses, nurse practitioners, physical therapists, lab technicians and the like. The healthcare practice can also include one or more treatment rooms 36, test facilities 37 and surgical theaters 40. Treatment rooms can include, for example, locations in which a physician consults with her patient, were treatment is given to the patient. Test facilities 37 can include facilities such as x-ray facilities, MRI facilities, treadmills, ultrasound equipment, and laboratories, just to name a few.

As would be apparent to one of ordinary skill in the art after reading this description, various different healthcare practices may use other internal or external resources 44, 45 in the course of their practice. These and the other described resources can be communicatively coupled to one another, for example, using networking technology. Accordingly, electronic records and other data can be shared among the various resources to facilitate performance of a given resource's determined functions. Also, as noted above, the resources can include computing capabilities used in performance of their tasks.

As described in more detail below, client computing devices with applications running thereon can be provided for use by personnel of the various resources to manage their tasks and responsibilities. These client computing devices can be handheld computing devices (e.g., tablet computers, iPads, smart phones, laptops, etc.) and can be communicatively linked to the healthcare provider network such that information (e.g. patient information, treatment information, prescription information, billing information, and so on) can be shared between the client devices and the various resources of the healthcare practice. In example embodiments discussed below, these client devices are described as handheld computing devices. However, after reading this description, one of ordinary skill in the art will understand how to implement the features and functionality described herein using desktop, wall-mounted, equipment-integrated, or other computing devices to perform the client computing functions.

A workflow management service 48 can be included with the healthcare practice to manage the data and information in the healthcare practice and to provide information to the client computing devices. In various embodiments, workflow management service 48 can be integrated with server 31 (e.g., an application running on server 31), it can be integrated with other computing resources in the healthcare facility, or it can be a stand-alone service with dedicated computing resources. workflow management service 48 can be configured to consolidate data and information from data storage facilities within healthcare facility (e.g., cloud storage 41, data storage 32, and data stored at various resources) as well as information received from sources external to the healthcare facility.

Workflow management service 48 can be configured to gather this information and provide it to the one or more client computing devices used in the healthcare facility. For example, in some embodiments, workflow management service 48 retrieves a predefined set of information (e.g. patient electronic health records, billing records, scheduling records, etc.) and provides this information to the client computing devices. The information can be tailored for one or more client computing devices or groups of client computing devices or all of the gathered information can be sent to the client computing devices. For example, particular pieces of information relevant to a resource with which a client computing device is associated can be culled from the full set of gathered information and send to that associated client computing device. As a further example, patient health records and scheduling information may be gathered and sent to one or more client computing devices used by physicians or other healthcare providers 39 in the healthcare facility. Still further, in facilities where there are multiple healthcare workers (for example, physicians), patient records can be gathered and sorted such that each physician receives only that information pertaining to his or her patients.

In various embodiments, the data can also be transmitted to insurance payors for claims processing. The data transmitted can include results or "outcome-focused" information about the patient's recovery as gathered by the application. This data, combined with the procedure and bracing information, can in some embodiments support and enhance the outcome of the patient through the orthopedic episode.

As another example, billing and scheduling information might be gathered and sent to the billing department 34. Accordingly, client computing devices (or applications running thereon) can be identified with specific personnel at the healthcare facility or with particular resources or functions of the healthcare facility. In this manner, tailored sets of information can be delivered to specific client computing devices to avoid the need to download all data to all devices. In some embodiments, the client computing devices are identified by information coded into the applications. In other embodiments, the client computing devices can be identified based on login information provided by healthcare worker. In this latter example, client computing devices can be shared amongst different practitioners, such, as for example, across different shifts.

As stated above, in the example healthcare practice, the various resources can each include computing capabilities and various client computing devices can be provided for use as well. In order for these devices to operate well and for the functions of the healthcare practice to be integrated, these devices can be configured to share information with one another as may be relevant to their respective resource functions.

Various embodiments of the systems and methods described herein are described with reference to the example environment of a healthcare facility set forth and described with reference to FIG. 1. After reading this description, it will become apparent to one of ordinary skill in the art how the systems and methods disclosed herein can be used in conjunction with other environments and other healthcare facilities. Additionally, for ease of discussion and to better illustrate features of the systems and methods disclosed herein, the various embodiments are described at times in the context of an example patient healthcare scenario. In this example scenario, a patient arrives at a physician's office (e.g., an office in the healthcare environment of FIG. 1) to receive treatment for a torn anterior cruciate ligament (ACL). In this example, the patient receives surgical treatment to repair or reconstruct the torn ACL; and after an appropriate healing time the health-care practitioner prescribes a knee brace and a physical therapy regimen. The physician, nurse practitioner, physical therapist, or other healthcare practitioner fits the patient with the appropriate brace and instructs the patient on the use of the brace. The healthcare practitioner also instructs the patient to perform prescribed physical therapy exercises, record his or her physical therapy activity, and report back to the healthcare practitioner with the results. Although the systems and methods disclosed herein are described at times in terms of this example healthcare-treatment scenario, after reading this description one of ordinary skill in the art will understand how the technology disclosed herein can be applied to other treatments scenarios or physical therapy regimens.

Figure 2:
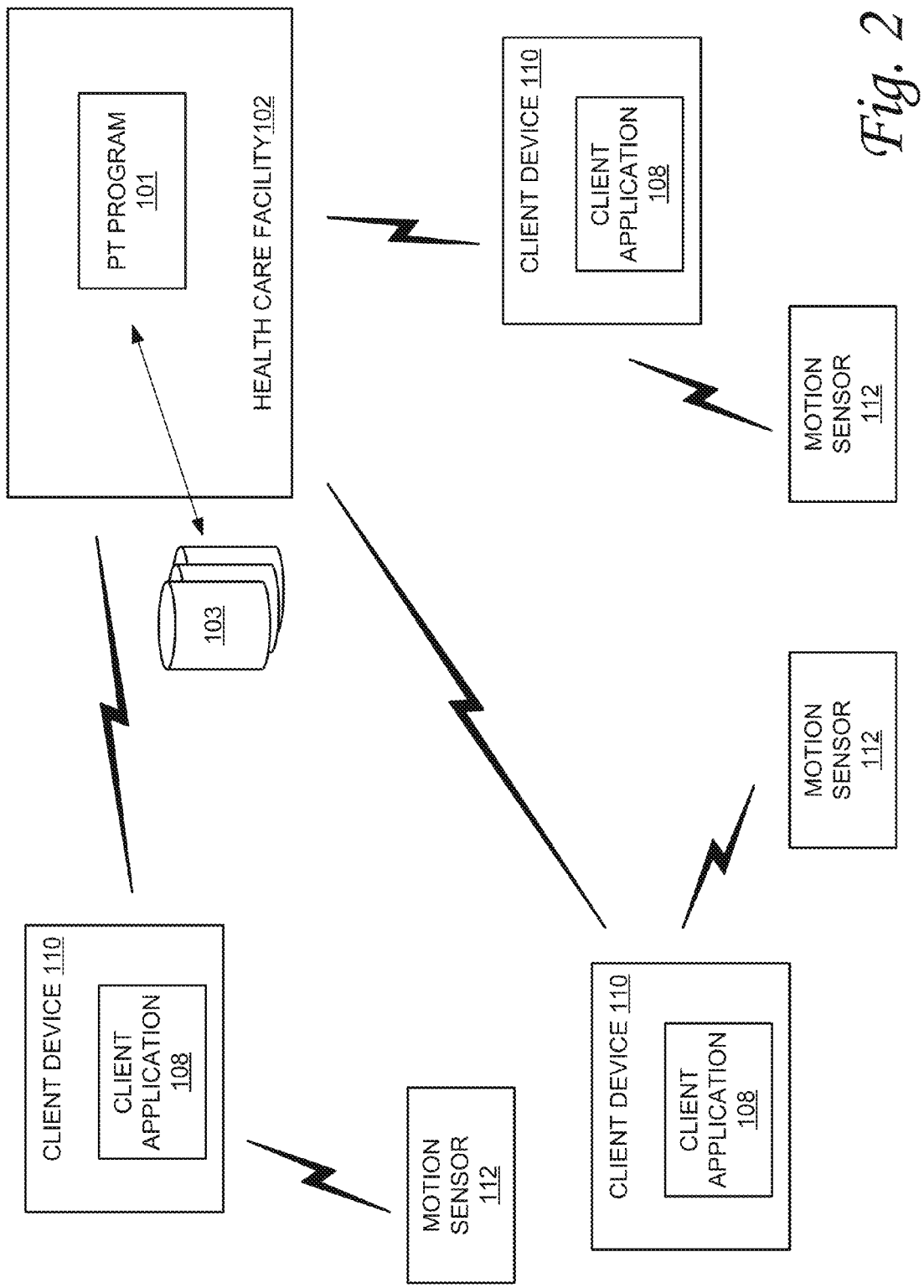
FIG. 2 is a high-level block diagram illustrating an example system for implementing an automated physical therapy program in accordance with various embodiments of the technology described herein.

FIG. 2 is a high-level block diagram illustrating an example system for implementing an automated physical therapy program in accordance with various embodiments of the technology described herein. Referring now to FIG. 2, in this example a physical therapy application program 101 is provided and configured to run on a computing device in a healthcare practitioner's office or other healthcare facility 102. The physical therapy application program 101 can be used by physicians or other health care providers to manage and control physical therapy for its patients. The physical therapy program can access various databases 103 and other resources, whether local or remote to the health care facility (including, e.g., cloud-based resources), to obtain information. The information can include, for example information about patients being treated, (including their illnesses or injuries and other electronic health records) physical therapy regimens, instructions for physical therapy regimens, and so on.

The patients are provided with a client physical therapy application 108, which the patients can download and run on their own client computing devices 110. Examples of client computing devices 110 can include tablet computers, iPads, personal computers, smart phones, and any of a number of other computing devices available to the patients. Client applications 108 can be used to instruct the client on the proper performance of the prescribed exercises or activities; instruct the patient on the number of reps and sets of the prescribed exercises and activities; trigger alarms or send reminders to the patient to remind the patient to perform the exercises or activities at the designated times or intervals; provide a graphical user interface to allow the user to interact with the application; provide visual feedback to the patient regarding performance of the exercise or activities; log or otherwise keep track of the patient's performance of the exercises or activities; create reports (including graphs; charts; tabular data and so on) of the patient's performance; and report the above information to the healthcare practitioner in real time or on a periodic basis.

In various embodiments, the patient is provided with one or more motion detection apparatus 112 that can be worn by the patient during the exercise. The motion detector in various embodiments can comprise componentry such as, for example, one or more accelerometers, motion sensors, optical sensors, communications devices, memory and so on. In various embodiments, the motion detection apparatus can be implement as the CC2541 SoC Sensor available from Texas Instruments, Post Office Box 655303, Dallas, Tex. 75265, although other apparatus can be utilized. The motion detection apparatus can be used in conjunction with application 108, as more fully described herein, to perform functions such as, for example, measuring the movement of the patient (e.g., measuring the swinging of the patient's leg), counting the number of repetitions and exercise interval, determining the speed and range of motion during exercise, measuring ambient exercise conditions (e.g., temperature, humidity, barometric pressure, etc.).

Motion detection apparatus 112 may also include a communications interface (preferably, a wireless communication interface) to allow the sensed information to be communicated to application 108. Similarly, client computing devices 110 are provided with the application interface to allow communication such as, for example, application download, receipt of information from motion sensors 112, and the provision of physical therapy information to automated physical therapy program 101. Accordingly, a variety of application interfaces can be provided and utilized including, for example, communication interfaces such as Bluetooth, Wi-Fi, Ethernet, cellular, and other wired or wireless communication interfaces.

Figure 3:
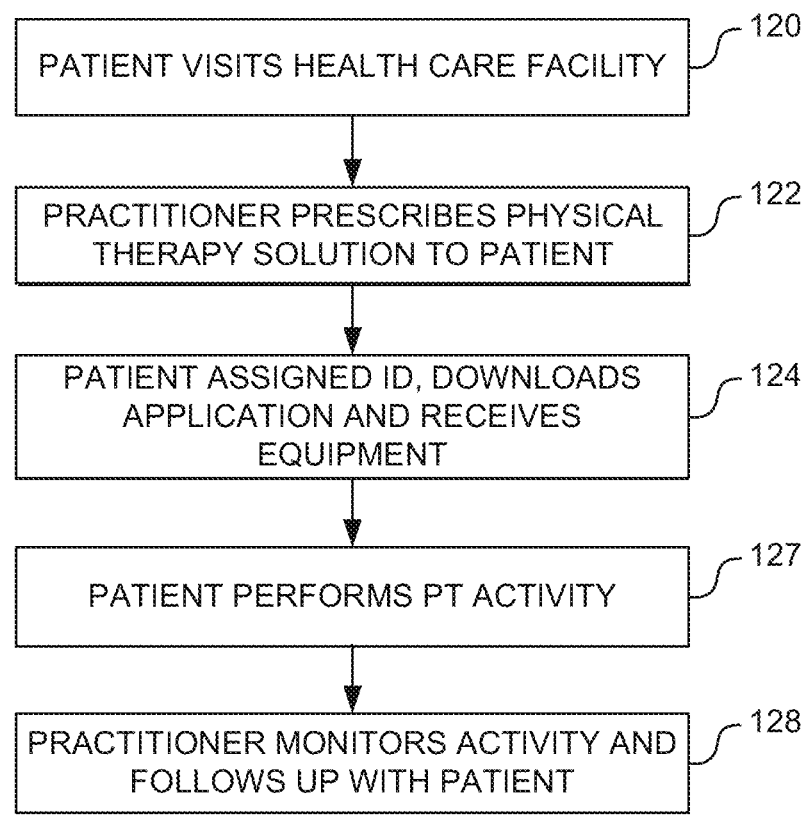
FIG. 3 is an operational flow diagram illustrating an example process for automated physical therapy in accordance with one embodiment of the technology disclosed herein.

FIG. 3 is an operational flow diagram illustrating an example process for automated physical therapy in accordance with one embodiment of the technology disclosed herein. Referring now to FIG. 3, at event 120, a patient visits the healthcare practice and is treated for an identified injury. For instance, in terms of the example described above, the patient with a torn ACL visits his or her physician and has surgery performed to repair or reconstruct the torn ACL.

At event 122, as part of the recovery process the healthcare practitioner prescribes an exercise regimen to assist in the recovery or rehabilitation of the patient. In terms of the example of the torn ACL, the patient may be given a series of leg, knee and ankle exercises to help strengthen the ACL post surgery and to restore the patient's range of motion. The healthcare practitioner may also prescribe the use of the knee brace to prevent further injury and provide control to allow the existing ACL injuries to heal.

The client computing device can include, for example, a processing device used by the patient to facilitate the physical therapy activity. For example, an iPad, smart phone, tablet computer, PC, or other computing device can be provided with an application to provide instructions to the patient regarding the physical therapy regimen, remind the patient to perform the activities prescribed in the physical therapy regimen, receive and log data from the motion sensor reflecting the patient's activity during the physical therapy regimen, and communicate information regarding the physical therapy to the patient's healthcare provider.

Accordingly, at step 124, the patient obtains the items used to track the physical therapy regimen. For example, the healthcare practitioner can provide the patient with an accelerometer, a pedometer, or other motion sensor that can be used, for example, as described above. The motion sensor can be worn by the patient during physical therapy activity. In some embodiments, motion sensor can be integrated in or attachable to the patient's brace (e.g. a leg brace in the example of the ACL surgery). In another embodiment, the motion sensor can be worn by the patient on an ankle or wrist band to track leg or arm movement, respectively. As these examples serve to illustrate, there are number of mechanisms by which the motion sensor can be affixed to the appropriate portion of the patient's body to track the desired movement. Additionally, in further embodiments, multiple motion sensors can be utilized.

The patient also obtains the appropriate application for his or her computing device so that the patient can be instructed on the appropriate activity, and the patient's physical therapy sessions can be monitored, logged, and provided to the healthcare practitioner. In various embodiments, when the application is downloaded by the patient using the patient identifying code, the prescribed physical therapy exercises are downloaded or enabled as well. Accordingly, the prescribed exercises for a particular patient can be provided the patient along with his or her application.

At operation 127, the patient uses the application and motion sensor when performing the exercises prescribed in the physical therapy regimen. The system can be configured such that when the application is launched and an exercise selected, the application connects to the sensor. In operation, the motion sensor tracks the movement of the user and this information is provided to the application. The application uses this information to measure and log patient performance, as well as to provide visual and other feedback to the patient through the graphical user interface. The information provided to the healthcare facility by the application can be used by the application for the healthcare practitioner to gauge the level of performance achieved by the patient.

At operation 128, the healthcare professional receives information from the application. This information includes details about the patient's physical therapy performance as sensed by the motion sensor and logged by the application. The healthcare practitioner can use this information to monitor the patient's performance and progress, and determine appropriate follow-on courses of action. For example, the physician can see whether a patient is performing the prescribed activity, as well as the patient's level of performance.

Figure 4:
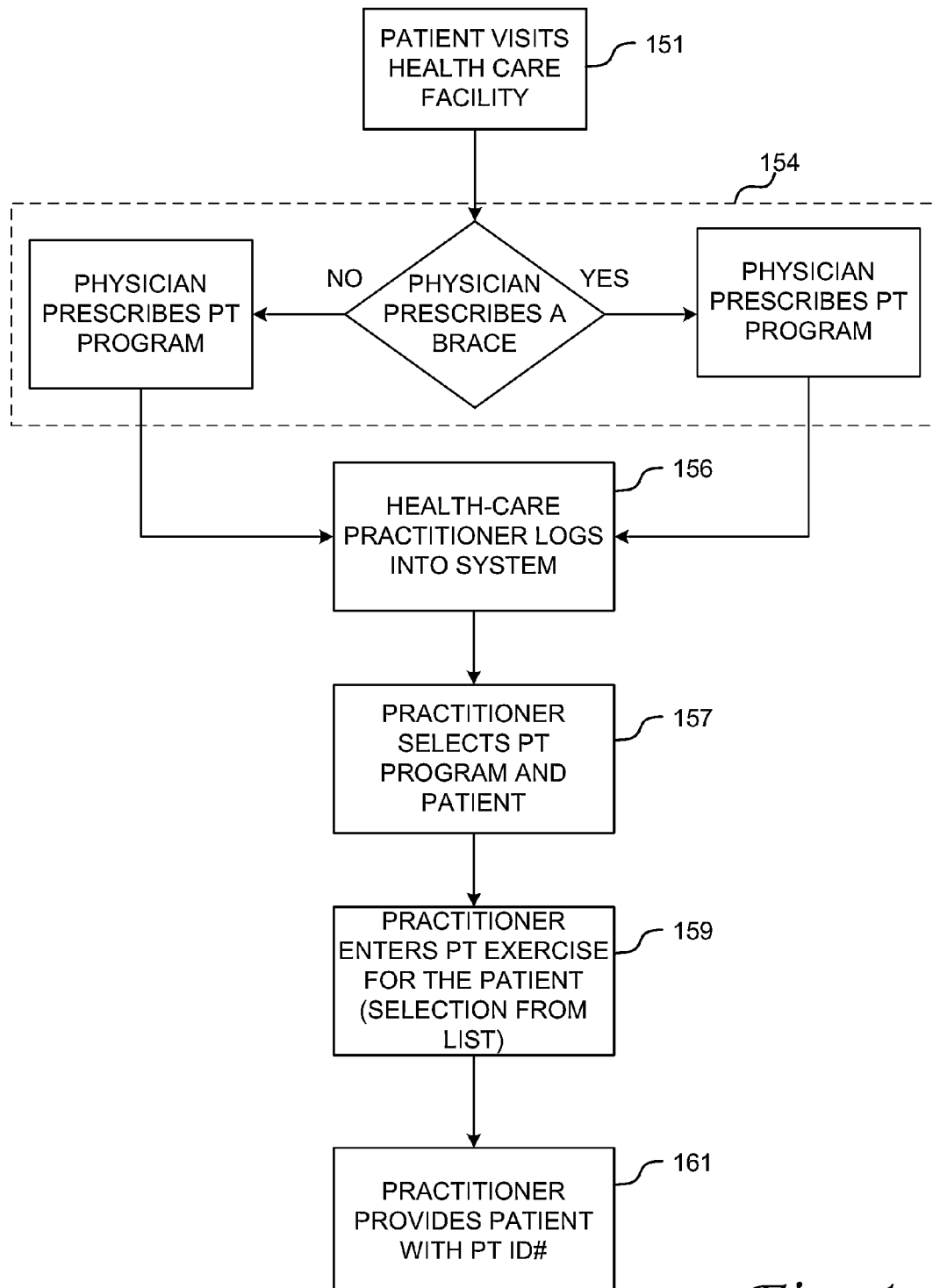
FIG. 4 is a diagram illustrating an example process for prescribing automated physical therapy treatment to a patient in accordance with one embodiment of the technology described herein.
Figure 5:
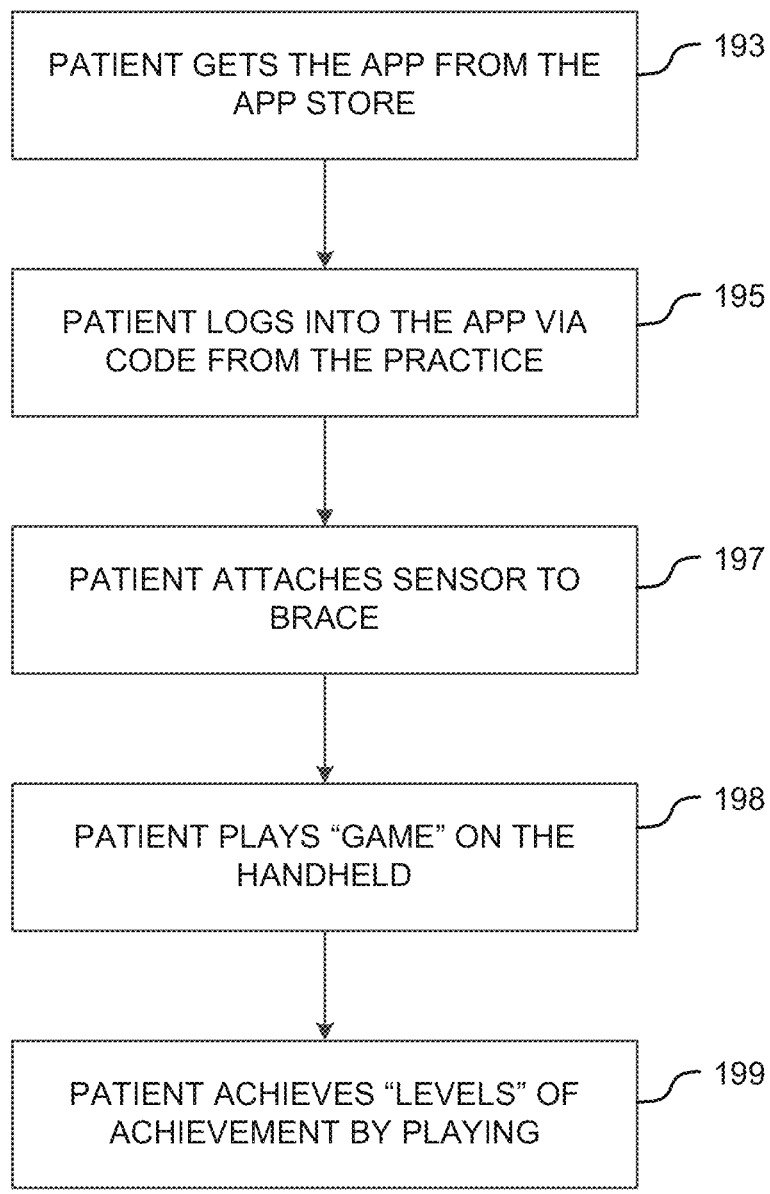
FIG. 5 is an operational flow diagram illustrating an example process of the patient obtaining and using the application (e.g. application 108) to perform the physical therapy routines.
Figure 6:
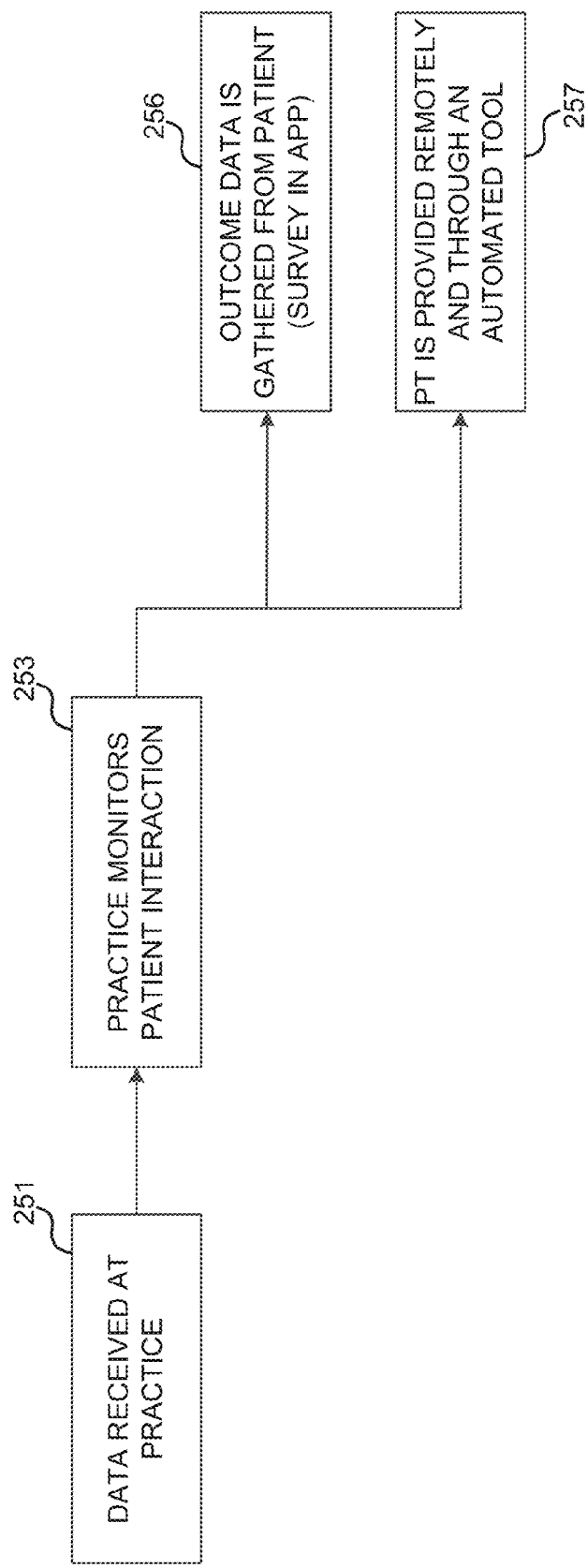
FIG. 6 is a diagram illustrating an example process for monitoring patient performance by the healthcare provider in accordance with one embodiment of the technology described herein.

FIGS. 4, 5 and 6 describe examples of the above process in greater detail. For instance, FIG. 4 is a diagram illustrating an example process for prescribing automated physical therapy treatment to a patient in accordance with one embodiment of the technology described herein. Referring now to FIG. 4, at event 151 a patient visits a clinic regarding a particular malady. For example, the patient may have a torn ACL and desires treatment. The physician or other healthcare practitioner meets with the patient, makes a diagnosis, and determines, as appropriate, a course of treatment. For example, the patient may require surgery to repair the torn ACL, or an alternative treatment path may be determined.

At operation 154, the healthcare practitioner determines an appropriate recuperative plan, which may include, for example, a recuperative therapy or other physical therapy regimen. The physical therapy regimen may involve one or more exercises or other activities intended to restore the patient's health or physical condition. In some instances, the patient may also require a brace (e.g., knee brace, elbow brace, etc.) to provide support to the injured joint.

At operation 156, the healthcare practitioner logs into an automated physical therapy system (e.g., automated physical therapy program 101) to initiate the process of setting up the patient's physical therapy regimen and prescribing a physical therapy program. At operation 157, the practitioner identifies the patient and obtains the patient's medical records. At operation 159, the practitioner selects or otherwise defines an appropriate physical therapy program for the patient considering the patient's injury and treatment objectives. In some embodiments, the automated physical therapy system may recommend to the healthcare practitioner particular physical therapy exercises that can be used for the patient's condition as indicated in the patient's records. The practitioner prescribes the physical therapy routine to the patient in the physical therapy program, and the system associates the prescribed physical therapy routine (e.g. one or more exercises or activities) with the patient. The practitioner may also decide to create a "custom" exercise using the disclosed technology. A custom therapy can be tailored to the specific patient and transmitted to the patient's home for use.

At operation 161, the practitioner provides the patient with a physical therapy ID number or other login information that the patient can use to retrieve his or her personalized physical therapy regimen via application 108. With these operations complete, the physical therapy regimen is prescribed, and the patient is able to download the application (if it's not already downloaded) login to the system and use the application to assist the patient in performing the exercises and keep track of the patient's progress and performance.

FIG. 5 is an operational flow diagram illustrating an example process of the patient obtaining and using the application (e.g. application 108) to perform the physical therapy routines. Referring now to FIG. 5, at step 193 the patient obtains the appropriate application. For example, in various embodiments, the patient downloads the application for his or her device from the appropriate app store or from the health care facility. In some embodiments, the user ID or a special key may be required to download the appropriate application and exercises for the patient's regimen. In other embodiments, the general automated physical therapy application can be downloaded and the appropriate routines subsequently provided to the patient by the application when the patient uses the app to log into the system.

At operation 195, the patient logs into the application using the login information provided by the healthcare practitioner. As stated above, the application downloaded may be already preloaded with the appropriate physical therapy regimen. In other embodiments, upon login, the application may be configured to access an appropriate server (e.g. a server at healthcare facility 102, or other appropriate server) and retrieve the prescribed physical therapy regimen.

At operation 197, the patient activates the motion sensor and affixes the motion sensor as instructed. For example, as described above, the motion sensor might be affixed to the patient's prescribed brace or otherwise worn by the patient. At operation 198, the patient initiates the application. The application may cause the client device 110 to synchronize with or otherwise enter into communication with motion sensor 112. The application provides instructions to the patient for the exercise or exercises to be performed. For example, in some embodiments, detailed instructions can be provided to the patient by the application. The application can provide animated instructions, audio/visual instructions, or other instructions to the user. The user follows the instructions and conducts the exercises as specified by the application.

In some embodiments, the exercises can be presented in the form of a game in which the patient is provided with goals and awarded points or other rewards for achieving this set forth goals. The goals can include for example a specified number of reps, a specified number of sets, achieving a range of motion, completion in a given timeframe, and so on. As described more fully below, in some embodiments, the application can be configured to provide a graphical or even animated representation of the exercises as actually being performed by the patient. As an example in terms of the ACL scenario, the application may provide an animation of a person in a seated position extending his or her leg, in which the application uses information provided by the motion sensor and causes the animation to move with motions corresponding to the actual movement performed by the user. Thus, by viewing the information on the screen, the patient can see a real-time representation of his or her actual movement as depicted by the character in the information. Other graphical features such as lines, bars, and so on can be used to show the patient goals for his or her range of motion, maximum range of motion achieved during exercise or during previous exercises, and other like information.

At operation 199, as alluded to above, the patient obtains levels of achievement for performing the prescribed regimen. For example, the patient may earn rewards points for achieving goals set forth by the healthcare practitioner or set forth in the prescribed regimen. In various embodiments, the rewards points can be used for a variety of different purposes. For example, the rewards points can merely be symbolic and used to reward the patient for his or her progress, while in other embodiments, the rewards points can be redeemable for or otherwise associated with actual rewards that can be attained. For example, in some embodiments the rewards can lead to monetary or other financially-related compensation. For example, in some embodiments, advertisers, merchants or other providers may participate in the process and may provide some form of compensation or other reward in exchange for reward points earned by the patient in performing the physical therapy routines. For example, in exchange for advertisement or other consideration, the providers may furnish prizes, cash, loyalty program points, discounts or coupons, gifts, or other compensation to the patient in exchange for achieving certain goals. Accordingly, various incentives can be built into the system to incentivize the patient to perform the prescribed exercises and achieve the desired goals.

FIG. 6 is a diagram illustrating an example process for monitoring patient performance by the healthcare provider in accordance with one embodiment of the technology described herein. Referring now to FIG. 6, at operation 251, the data associated with the patient's physical therapy regimen is sent by the patient to the healthcare provider and received at the healthcare provider's office. For example, the exercise data can be sent from application 108 to automated physical therapy program 101 at healthcare facility 102.

At operation 253, the healthcare practice receives the data and logs it into the patient's file. The data can be sent with identifying information that can be used to identify the patient to which the data corresponds. This enables the data to be associated with the appropriate records in the database. Real-time or periodic alerts can be provided to the practice informing them of the receipt of the data. In some embodiments, the patient's healthcare practitioner is identified in the database as well, and the practitioner can be alerted or notified of the receipt of the data. Alerts can also be generated by the client application 108 and sent to the practitioner (e.g. directly or by way of automated physical therapy program 108 alerting the practitioner of completed exercises or when exercises are missed or only partially completed.

Alerts can be in the form of text messages, e-mails, phone calls, a flag on the GUI of the practitioners computing system, or other alert sufficient to notify the practitioner that the data has been received. The practitioner can then review the data and check on the patient's performance. If the patient is underperforming, the healthcare practitioner can call or schedule an appointment with the patient to review progress, determine if the patient is having difficulties or problems that need to be addressed, or simply to remind the patient to try harder when performing the routines. Where the patient is performing well, the practitioner may reach out and congratulate the patient, and, in some embodiments, the practitioner may have the ability to award the patient with rewards points or additional rewards points for good performance. Importantly, the practitioner uses the information to determine the progress of the patient and to determine whether a change needs to be made in the prescribed physical therapy regimen or if other follow-up treatments are required.

As illustrated in the example of FIG. 6, the patient applications 108 can also be configured to survey the patients for various purposes. This is illustrated at operation 256. For example, outcome data for a plurality of patients can be gathered for each of the different physical therapy regimens that have been prescribed for particular conditions. The efficacy of these treatments can be determined based on the survey information and this information can be used to refine treatment or to identify treatments that work better than others. The survey information can be in the form of questions posed to the patient, and the patient's responses can be used to gauge the success of the physical therapy head regimen.

In other embodiments, actual results achieved, as measured by the physical therapy monitoring system, can be used as a metric to determine the efficacy of treatment. For example, the times required for a patient to achieve a particular range of motion can be used to determine, at least to some extent, the speed of the patient's recovery, and therefore the efficacy of the treatment. In yet other embodiments, both questionnaire information and measured performance information can be used for purposes of the survey. This is just one example, and the survey is not limited to determining the efficacy of one or more treatment options. Indeed, the survey can be used for a number of different purposes to gather information about the physical therapy routines. This can include, for example, information regarding patient preferences, exercises that appear to be performed more regularly than others, and so on.

As shown at block 257, using the technology described herein, the physical therapy can be provided remotely using these automated tools. Although not mentioned above, in various embodiments, real-time practitioner-patient interaction can take place through the applications described herein. For example, the doctor or patient can initiate a video or audio phone conference to discuss topics such as the patient's health and condition, the exercise routines, and so on. The doctor or patient can take advantage of a live video conversation to monitor the patient's performance and provide feedback. Likewise, as described in more detail below, photographs and other information can be captured and provided with the data to provide the healthcare practitioner with additional information regarding the patient's performance.

In various embodiments, as described above graphical user interfaces, or GUIs, are used to allow the patient to interact with the client application 108. The systems and methods described herein are not dependent on any particular form of GUI, and any of a number of GUIs can be created and implemented to gather the appropriate information, informed the patient, and provide the desired patient experience. FIGS. 7 through 10 provide one example of portions of a graphical user interface that is suitable for use with the systems and methods described herein.

Figure 7:
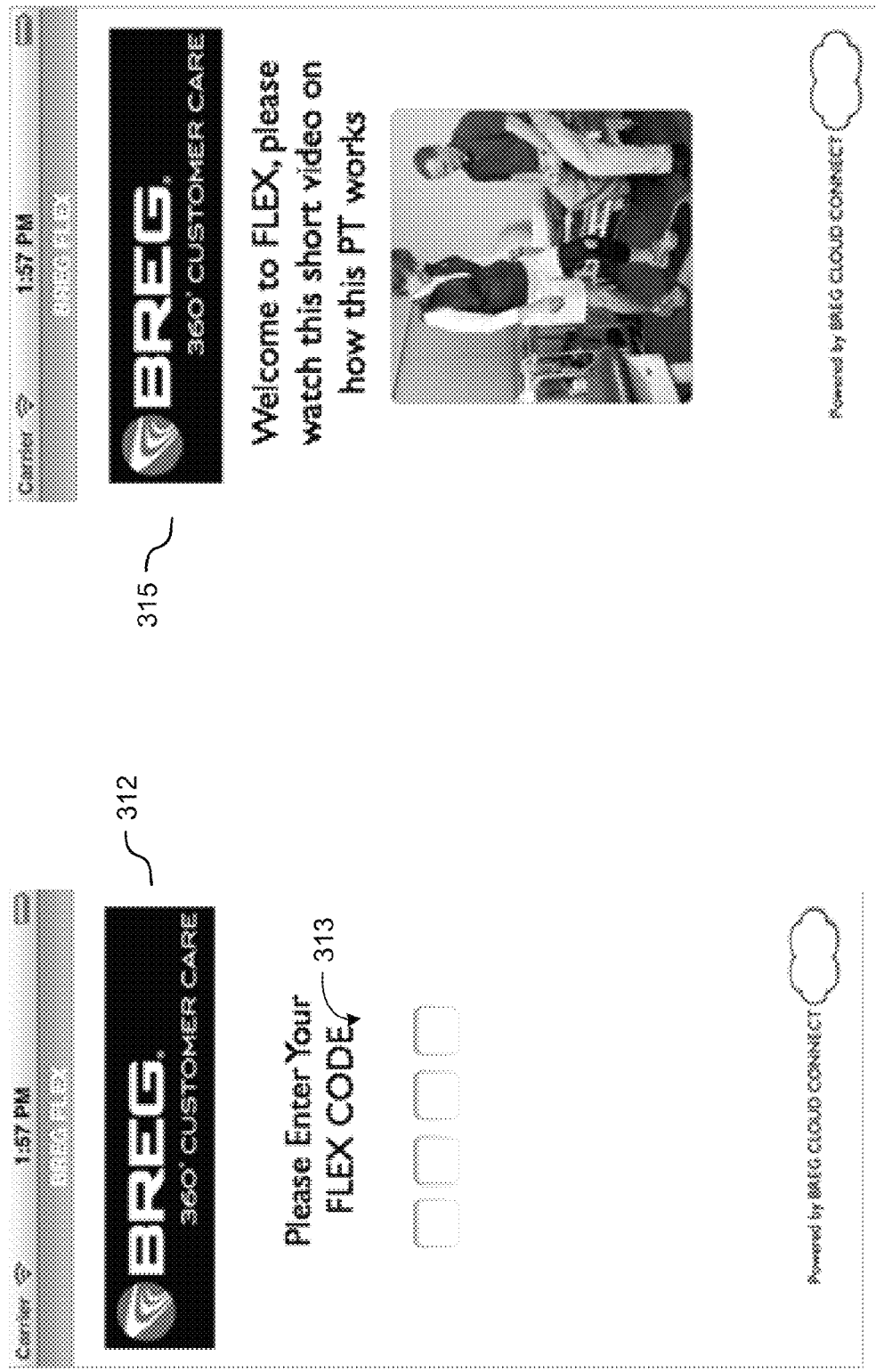
FIGS. 7 through 10 provide one example of portions of a graphical user interface that is suitable for use with the systems and methods described herein. These figures also demonstrate the capability for the software to support outcome management for an individual patient or a collection of patients under the care of the practitioner(s) that is monitoring the system.

Referring now to FIG. 7, screen 312 provides an example of an opening a login screen that can be presented to the patient. As noted above, to initiate the automated physical therapy process, the patient downloads and installs the application (for example a mobile application) for the at-home physical therapy. Once installed and opened, a login screen is presented providing the patient with the opportunity to enter his or her identification code as provided by the healthcare facility. In the illustrated embodiment, a 4-character identification code 313 is shown, however, other identification codes can be used including codes comprising alphanumeric characters, fingerprint sensors, facial recognition, or other identification information. Additionally, a username can be required as well as secondary challenges such as patient zip code or other patient information that can be entered to verify the patient's identity.

With continued reference to FIG. 7, GUI 315 illustrates an example GUI they can be used to provide additional information to the patient. This GUI presents a video to the user that allows the user to view one or more videos regarding the physical therapy process. For example, in some embodiments a video for first-time users is provided to introduce the process to the user and provide the patient with instructions he or she may need to utilize the system, connect with the motion sensor, or to obtain maximum value from the system. Additionally, one or more videos showing the patient how to perform his or her exercise routines can also be provided. The videos can be prerecorded videos used for a number of patients to provide general instruction regarding the system or specific instruction regarding the exercises. Additionally, the healthcare practitioner can record personalized or patient-specific videos for the patient and the videos can be retrieved and downloaded by the application 108 when the patient logs into the system. In this manner, a more personalized approach can be provided through the GUI.

Figure 8:
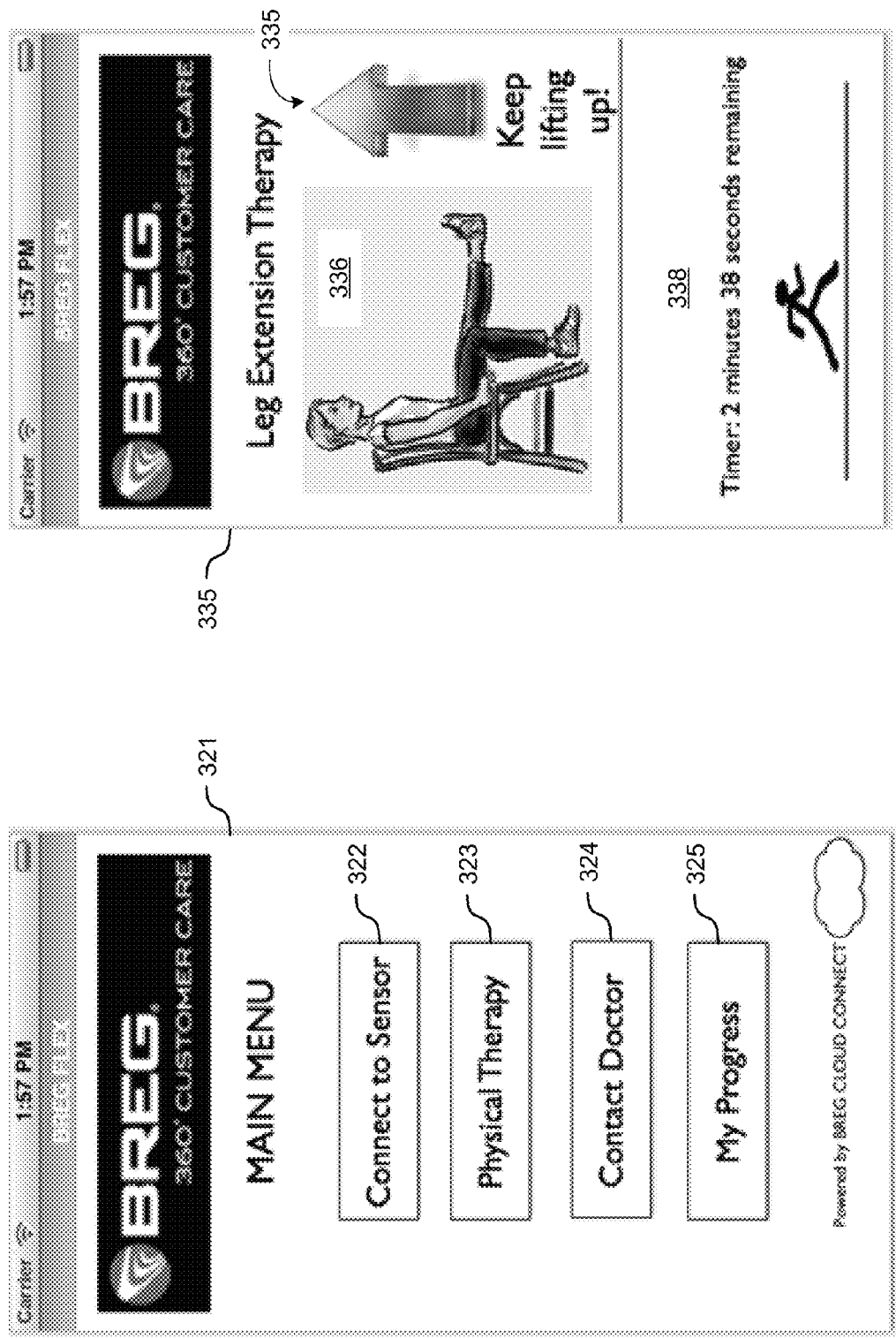

Referring now to FIG. 8, screenshot 321 provides an example of the main menu that can be presented to the user as a starting point for the application. As illustrated in this example, the main menu includes buttons to allow the user to select various features of the system these include a Connect To Sensor button 322, Physical Therapy button 323, a Contact Doctor button 324, and a My Progress button 325.

Figure 9:
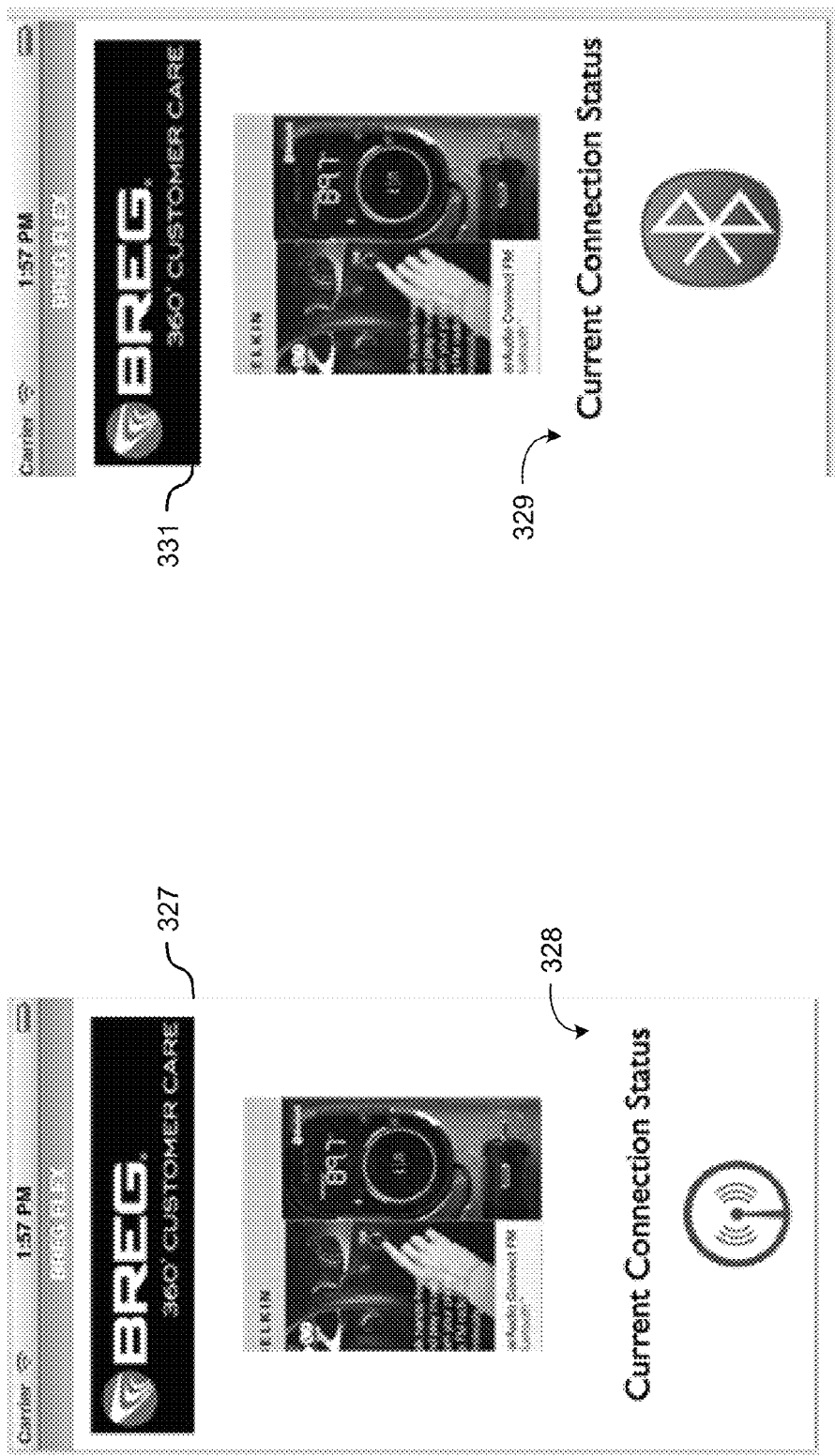

Connect To Sensor button 322 can be used at the beginning of the session to allow the application 108 and the client device 110 to connect to the motion sensor 112. In some embodiments, a connection can be automatic when the application is launched thereby avoiding the need for the patient to manually initiate the process. In still further embodiments, when Connect To Sensor button 322 is selected, a video is presented to the user instructing the user how to connect the sensor to the application. An example of this is shown by screen 327 (FIG. 9). Screen 327 also shows the current connection status. For example, icon 328 may appear when the application is connected or it may change color to show connection status—e.g., blue for connected, and red for disconnected. Additionally, in some embodiments, the icon may change indicating the connection status. For example, in the screen shot 331 shown in FIG. 9, a different icon 329 is provided to indicate connection of the sensor.

Referring back to FIG. 8, Button 323, when actuated, causes the application to enter the physical therapy mode. In this mode, the prescribed exercise or exercises are retrieved and the screens associated with those exercises are provided to the user. In some embodiments, the user can be given a menu of different exercises from which he or she may choose. In other embodiments, the exercises may be presented in an order as scheduled by the prescribing healthcare practitioner.

The user may also be provided with the option to view instructional videos or otherwise retrieve information about the physical therapy exercise selected. Screenshot 335 in FIG. 8 illustrates an example animation that is used to guide the patient through a given exercise. In the example illustrated in FIG. 8 using screenshot 335, the example is that of a leg-extension-therapy exercise. In this example, an animation 336 is provided to present to the patient a representation of the exercise he or she is performing in real-time. As the patient flexes and extends her leg, the motion sensor 112 senses this motion and provides information about this motion to application 108. As the patient flexes and extends her leg, the graphical representation 1 and GUI 335 is caused to flex and extend her leg in synchronization with the patient.

As illustrated in FIG. 8, the patient in the animation is shown in a still frame with her leg almost fully extended. Also shown in GUI 335 is an example of coaching or other instructional information 337 they can be provided to the patient when performing his or her exercises. As shown in the example of FIG. 8, informational message 337 in the screenshot is instructing the patient to keep lifting her leg up. This is an indication that her leg is not yet extended to the full extent desired for the prescribed exercise, and that she should keep lifting or try to keep raising her leg further. When the target extension has been reached, informational message 337 can change to illustrate to the user the next desired operation such as, for example, "Bend Your Knee and Lower Your Leg."

Figure 10:
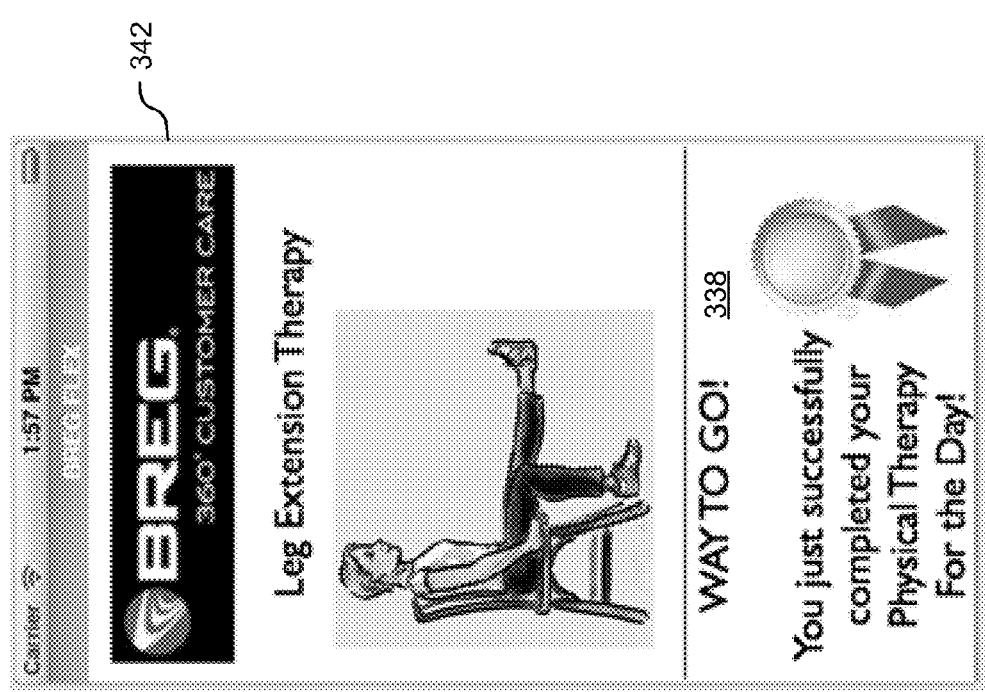

Also illustrated in the example of FIG. 8 is an area of the screen for exercise status 338. In the example illustrated in FIG. 8, status area 338 shows the time remaining for the exercise. Depending on the exercise or the goals of the exercise, status area 338 can show other information such as, for example, the number of reps completed and remaining or other information. Shown in FIG. 10 is example screen 342, in which progress message 338 can also show when the exercises successfully completed. In this example, the patient is informed that he or she successfully completed physiotherapy session and a ribbon is displayed as emblematic of success.

Referring again to FIG. 8, on the main menu selection of the Contact Doctor button 324 facilitates patient contact with the doctor. For example, in one embodiment the healthcare facility contact information, including Dr. contact information can be displayed to the user. In another embodiment, pressing the Contact Doctor button 324 causes the application to contact the healthcare facility or the attending practitioner correctly. This can open an e-mail or text message communication link, a telephone (e.g. cellular) communication link, a video-phone communication link or other communication link with the healthcare provider.

My Progress button 325 can be used to launch the portion of the application providing feedback to the patient regarding his or her progress through the physical therapy program. For example, captured and stored information can be provided to the patient regarding completed exercises, patient performance measured against prescribed goals, patient performance measured against population norms, and so on. The information can be provided in tabular, graphical, or alphanumeric form. Additionally, information regarding patient achievements and rewards can be accessed through the My Progress feature.

Figure 11:
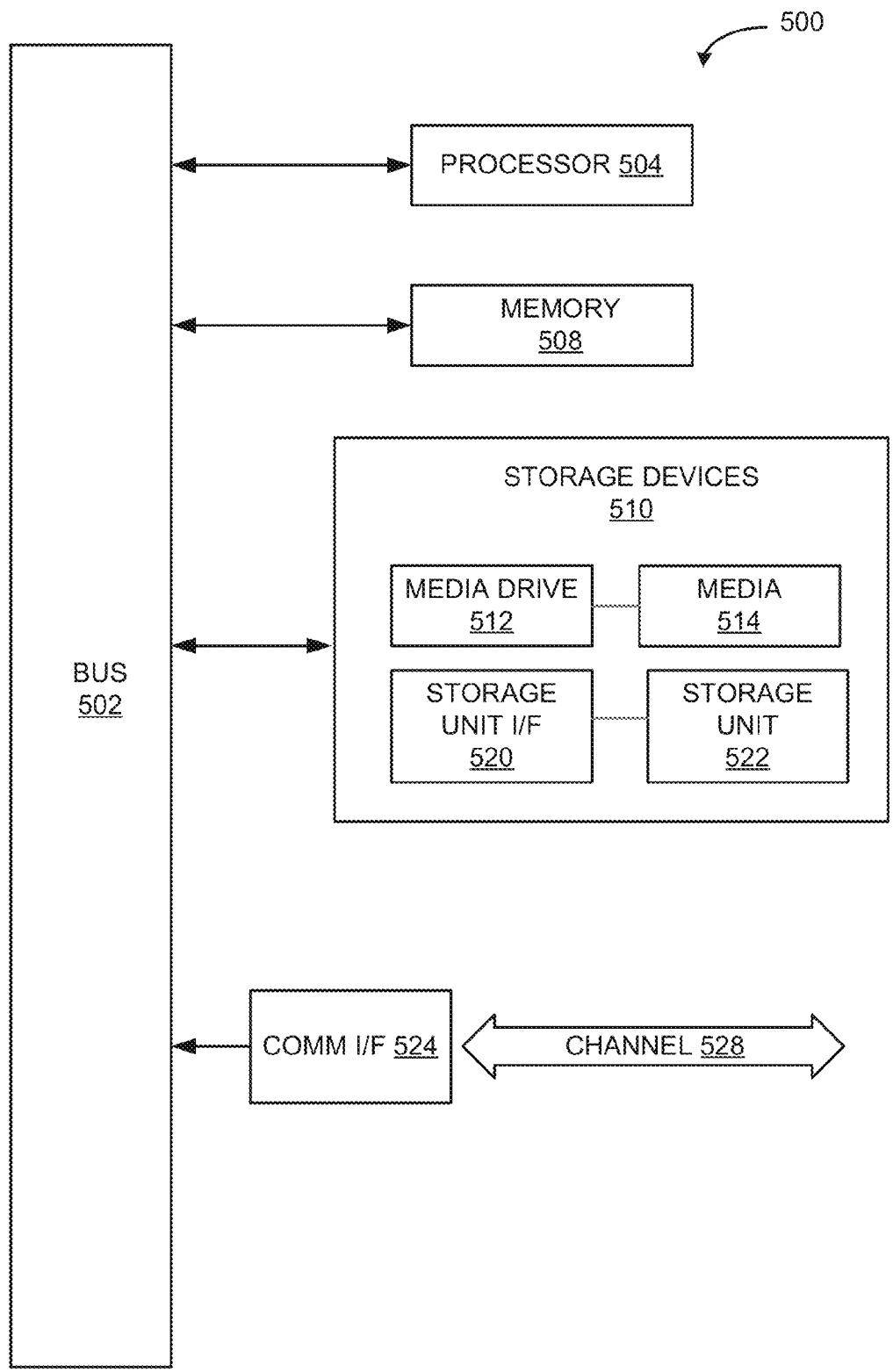
FIG. 11 is a diagram illustrating and example computing module in that can be used accordance with one embodiment of the technology described herein.

As used herein, the term module might describe a given unit of functionality that can be performed in accordance with one or more embodiments of the technology disclosed herein. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the technology are implemented in whole or in part using software, in one embodiment, these software elements can be implemented to operate with a computing or processing module capable of carrying out the functionality described with respect thereto. One such example computing module is shown in FIG. 11. Various embodiments are described in terms of this example-computing module 500. After reading this description, it will become apparent to a person skilled in the relevant art how to implement the technology using other computing modules or architectures.

Referring now to FIG. 11, computing module 500 may represent, for example, computing or processing capabilities found within desktop, laptop and notebook computers; hand-held computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 500 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 500 might include, for example, one or more processors, controllers, control modules, or other processing devices, such as a processor 504. Processor 504 might be implemented using a general-purpose or special-purpose processing engine such as, for example, a microprocessor, controller, or other control logic. In the illustrated example, processor 504 is connected to a bus 502, although any communication medium can be used to facilitate interaction with other components of computing module 500 or to communicate externally.

Computing module 500 might also include one or more memory modules, simply referred to herein as main memory 508. For example, preferably random access memory (RAM) or other dynamic memory, might be used for storing information and instructions to be executed by processor 504. Main memory 508 might also be used for storing temporary variables or other intermediate information during execution of instructions to be executed by processor 504. Computing module 500 might likewise include a read only memory ("ROM") or other static storage device coupled to bus 502 for storing static information and instructions for processor 504.

The computing module 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a floppy disk drive, a magnetic tape drive, an optical disk drive, a CD or DVD drive (R or RW), or other removable or fixed media drive might be provided. Accordingly, storage media 514 might include, for example, a hard disk, a floppy disk, magnetic tape, cartridge, optical disk, a CD or DVD, or other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing module 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory module) and memory slot, a PCMCIA slot and card, and other fixed or removable storage units 522 and interfaces 520 that allow software and data to be transferred from the storage unit 522 to computing module 500.

Computing module 500 might also include a communications interface 524. Communications interface 524 might be used to allow software and data to be transferred between computing module 500 and external devices. Examples of communications interface 524 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 524 might typically be carried on signals, which can be electronic, electromagnetic (which includes optical) or other signals capable of being exchanged by a given communications interface 524. These signals might be provided to communications interface 524 via a channel 528. This channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 500 to perform features or functions of the disclosed technology as discussed herein.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. An automated physical therapy system for providing automated exercise management, comprising:
   a mounting device configured to be attached in a fixed position on a movable member of a patient's body during performance of a prescribed exercise routine;
   a motion sensor attached to the mounting device and configured to sense motion during performance of the prescribed exercise routine and to wirelessly communicate movement data representative of the sensed motion during performance of the prescribed exercise routine;
   a physical therapy non-transitory memory in which is stored a library of files related to exercise therapy, wherein the files of the exercise therapy library comprise a video for a first time user to introduce the therapy process and to provide a user with general instructions needed to utilize the physical therapy system, a plurality of files having prerecorded video therapy exercise routines not specific to any particular patient, each of which contains specific instructions regarding an exercise, a patient-specific video showing a patient performing a custom exercise for a custom therapy both of which have been tailored for a particular patient;
   a patient non-transitory memory in which is stored a database of patients, the database having at least one of patient identification, a list of at least one authorized health care practitioner (HCP) for a patient, and a prescription for therapy exercise routines issued by an HCP, wherein the prescription requires the patient to perform exercise routines in a particular order;
   a server programmed to access the physical therapy memory and the patient memory to verify patient identification, to verify health care practitioner ("HCP") identification, to access a patient's prescription, and in accordance with the prescription to download therapy exercise files including videos for general exercises and a patient-specific video having a custom exercise after receipt of that patient's identification and prescription verification;
   an HCP computing device programmed to communicate with the server to provide HCP identification, to request access to a particular patient's therapy prescription, to store a link to a pre-recorded video therapy exercise routine file and a link to a custom exercise in the physical therapy memory, and to store a prescription having a list containing an order in which the linked exercise routine files are to be performed by the patient; and
   a patient computing device having a patient wireless communication interface configured to wirelessly receive movement data from the motion sensor, the patient computing device also comprising a display device, and a patient computing device memory in which is stored an automated physical therapy application, and a patient device processor being programmed by the stored automated physical therapy application to automatically communicate with the server to identify a patient and to control the display device to present a menu of videos available to the patient for downloading and running in the order specified by the prescription, and in response to a patient's selection from the menu, to download and run a selected therapy video exercise file linked to the patient in the patient database, in the order listed in the prescription, receive movement data from the motion sensor worn by the patient as the patient performs the exercise being run, control the display device to present an animation of the patient performing the downloaded exercise, process the movement data and control the display device to coach the patient to perform the exercise properly as prescribed and prepare and upload patient performance data of the exercise to the server to be stored in the patient database.

2. The automated physical therapy system of claim 1 wherein the patient computing device processor is further programmed to download the automated physical therapy application from the server if the application is not resident in the patient computing device memory.

3. The automated physical therapy system of claim 1 wherein the mounting device comprises a brace to be worn on the movable member by the user during the prescribed exercise routine, wherein the motion sensor is attached to the brace during performance of the prescribed exercise.

4. The automated physical therapy system of claim 1 wherein the automated physical therapy application further programs the processor of the patient computing device to compare the movement data received from the motion sensor to the exercise routine to measure patient performance of the exercise routine against at least one of patient's prescribed goals and against population norms.

5. The automated physical therapy system of claim 1 wherein the automated physical therapy application further programs the processor of the patient computing device to automatically send information about the patient's performance as sensed by the motion sensor and logged by the automated physical therapy application to a health care practitioner who is associated with a patient in the patient memory.

6. The automated physical therapy system of claim 1 wherein the automated physical therapy application further programs the processor of the patient computing device to display on the display device of the patient computing device a button which, when pushed, is programmed to contact a health care practitioner ("HCP") by at least one of telephone, text message, e-mail, and video-phone.

7. A method of physical therapy management, comprising:
mounting a motion sensor to a mounting device, the mounting device adapted to be attached in a fixed position on a movable member of a patient's body during performance of a prescribed exercise routine, wherein the motion sensor is configured to sense motion during performance of the prescribed exercise routine and wirelessly communicates movement data representative of the sensed motion during performance of the prescribed exercise routine;
storing in a physical therapy non-transitory memory a library of files related to exercise therapy, wherein the files of the exercise therapy library comprise a video for a first time user to introduce the therapy process and to provide a user with general instructions needed to utilize the physical therapy system, a plurality of files having prerecorded video therapy exercise routines not specific to any particular patient, each of which contains specific instructions regarding an exercise, a patient-specific video showing a patient performing a custom exercise for a custom therapy both of which have been tailored for a particular patient;
storing in a patient non-transitory memory in which is stored a database of patients, the database having at least one of patient identification, a list of at least one authorized health care practitioner (HCP) for a patient, and a prescription for therapy exercise routines issued by an HCP, wherein the prescription requires the patient to perform exercise routines in a particular order;
programming a server to access the physical therapy memory and the patient memory to verify patient identification, to verify health care practitioner ("HCP") identification to access a patient's prescription, and in accordance with the prescription, to download therapy exercise files including videos for general exercises and a patient-specific video having a custom exercise after receipt of that patient's identification and prescription verification;
programming an HCP computing device to communicate with the server to provide HCP identification, to request access to a particular patient's therapy prescription, to store a link to a pre-recorded video therapy exercise routine file and a link to a custom exercise in the physical therapy memory, and to store a prescription having a list containing an order in which the linked exercise routine files are to be performed by the patient; and
programming a processor of a patient computing device with an automated physical therapy application to automatically communicate with the server to identify a patient and to control a display device to present a menu of videos available to the patient for downloading and running in the order specified by the prescription, and in response to a patient's selection from the menu, downloading and running a selected therapy video exercise file linked to the patient in the patient database, in the order listed in the prescription; and
further programming the processor of the patient computing device to wirelessly receive movement data from the motion sensor, as the patient performs the exercise being run, controlling the display to present an animation of the patient performing the downloaded exercise, processing the movement data and controlling the display to coach the patient to perform the exercise properly as prescribed and preparing and uploading patient performance data of the exercise to the server to be stored in the patient database.

8. The method of physical therapy management of claim 7 further comprising programming the processor of the patient computing device to download the automated physical therapy application from the server if the application is not resident in the patient computing device memory.

9. The method of physical therapy management of claim 7 wherein the step of mounting the motion sensor to a mounting device comprises mounting the motion sensor to a brace worn on the movable member by the user during the prescribed exercise routine.

10. The method of physical therapy management of claim 7 further comprising programming the processor of the patient's computing device to compare the movement data received from the motion sensor to the exercise routine to measure patient performance of the exercise routine against at least one of patient's prescribed goals and against population norms.

11. The method of physical therapy management of claim 7 further comprising programming the processor of the patient's computing device to automatically send information about the patient's performance of an exercise as sensed by the motion sensor and logged by the automated physical therapy application to a health care practitioner who is associated with a patient in the patient memory.

12. The method of physical therapy management of claim 7 further comprising programming the processor of the patient's computing device to display on the patient's display device a button which, when pushed, is programmed to contact a health care practitioner ("HCP") by at least one of a telephone, text message, e-mail, and video-phone.

* * * * *